United States Patent
Brueckner et al.

(10) Patent No.: US 10,018,644 B2
(45) Date of Patent: Jul. 10, 2018

(54) CARTRIDGE FOR DISPENSING A FLUID, AUTOMATIC ANALYZER AND METHOD OF ANALYZING A BIOLOGICAL SAMPLE

(71) Applicants: Roche Diagnostics Operations, Inc., Indianapolis, IN (US); Hitachi High-Technologies Corporation, Minato-ku (JP)

(72) Inventors: Thorsten Brueckner, Schriescheim (DE); Christoph Boehm, Viernheim (DE); Juergen Spinke, Lorsch (DE); Terumi Tamura, Ibaraki (JP); Taku Sakazume, Ibaraki (JP); Kyoko Imai, Minatoku (JP)

(73) Assignees: Roche Diagnostics Operations, Inc., Indianapolis, IN (US); Hitachi High-Technologies Corporation, Tokyo (JP)

( * ) Notice: Subject to any disclaimer, the term of this patent is extended or adjusted under 35 U.S.C. 154(b) by 379 days.

(21) Appl. No.: 15/006,476

(22) Filed: Jan. 26, 2016

(65) Prior Publication Data
US 2016/0139164 A1    May 19, 2016

Related U.S. Application Data

(63) Continuation of application No. PCT/EP2014/065482, filed on Jul. 18, 2014.

(30) Foreign Application Priority Data

Aug. 7, 2013    (EP) .................................... 13179523

(51) Int. Cl.
*B01L 3/00* (2006.01)
*G01N 35/10* (2006.01)
*B01L 3/02* (2006.01)

(52) U.S. Cl.
CPC ........ *G01N 35/1002* (2013.01); *B01L 3/0268* (2013.01); *B01L 3/0286* (2013.01);
(Continued)

(58) Field of Classification Search
USPC ............ 422/505, 522; 222/209, 211, 1, 207, 222/383.1
See application file for complete search history.

(56) References Cited

U.S. PATENT DOCUMENTS 4,392,860 A  *  7/1983  Huck .................... A61M 27/00
                                                                604/212
5,947,167 A      9/1999  Bogen et al.
(Continued)

FOREIGN PATENT DOCUMENTS

DE      19943121 A1    3/2001
EP       1959257 A2    8/2008
(Continued)

OTHER PUBLICATIONS

International Search Report dated Oct. 10, 2014, in Application No. PCT/EP2014/065482, 3 pages.
(Continued)

*Primary Examiner* — Erik B Crawford
(74) *Attorney, Agent, or Firm* — Woodard, Emhardt, Moriarty, McNett & Henry LLP

(57) ABSTRACT

A cartridge for dispensing a fluid is presented. The cartridge comprises a reservoir chamber for receiving the fluid. The reservoir chamber has a fluid outlet. The cartridge further comprises a controllable dispenser component for dispensing a dispensing volume of the fluid from the reservoir chamber. The dispenser component is connected to the fluid outlet of the reservoir. The cartridge further comprises a single compressible fluid pump with a single elastic pumping element and a conduit extending from the fluid pump
(Continued)

towards the fluid outlet. The fluid pump discharges a mixing volume of the fluid from the conduit into the reservoir chamber upon compression of the elastic pumping element. The mixing volume depends on the degree of compression of the elastic pumping element. The fluid pump sucks in the mixing volume from the reservoir into the conduit upon decompression of the elastic pumping element.

17 Claims, 6 Drawing Sheets

(52) U.S. Cl.
CPC ...... *G01N 35/1009* (2013.01); *B01L 2200/04* (2013.01); *B01L 2200/0684* (2013.01); *B01L 2300/0609* (2013.01); *B01L 2300/0832* (2013.01); *B01L 2300/123* (2013.01); *B01L 2400/0481* (2013.01); *B01L 2400/082* (2013.01)

(56) References Cited

U.S. PATENT DOCUMENTS

| | | | |
|---|---|---|---|
| 6,289,784 B1 * | 9/2001 | Park | B05B 11/00 222/209 |
| 8,318,109 B2 | 11/2012 | Saltsman et al. | |
| 2004/0265185 A1 | 12/2004 | Kitagawa | |
| 2010/0015009 A1 | 1/2010 | Wallace et al. | |
| 2011/0030760 A1 | 2/2011 | Meier et al. | |

FOREIGN PATENT DOCUMENTS

| | | |
|---|---|---|
| WO | 2005/016534 A1 | 2/2005 |
| WO | 2007/122387 A2 | 11/2007 |

OTHER PUBLICATIONS

Struele, W. et al., PipeJet: A Simple Disposable Dispenser for the Nano- and Microliter Range, Journal of The Association for Laboratory Automation, 2004, pp. 300-306, vol. 9.

* cited by examiner

US 10,018,644 B2

CARTRIDGE FOR DISPENSING A FLUID, AUTOMATIC ANALYZER AND METHOD OF ANALYZING A BIOLOGICAL SAMPLE

CROSS-REFERENCE TO RELATED APPLICATIONS

This application is a continuation of PCT/EP2014/065482, filed Jul. 18, 2014, which is based on and claims priority to EP 13179523.9, filed Aug. 7, 2013, which is hereby incorporated by reference.

BACKGROUND

The present disclosure generally relates to the field of fluidics and, in particular, to cartridges for dispensing microfluidic portions of fluids for the purpose of performing an analysis of a biological sample.

In medical laboratories, in vitro diagnostics are commonly performed on biological samples. Such tests may be performed manually using pipettes or maybe performed using an automatic analyzer. Automatic analyzers may automatically add reagents to the biological sample and may measure one or more physical properties of the biological sample during analysis. Automatic analyzers are known in the prior art. For example, one such automatic analyzer includes a reagent cassette holding mechanism for holding a plurality of reagent cassettes. Another analyzer has a reagent pipettor. The reagent pipettor is used for dispensing a reagent into a vessel containing a sample to initiate a chemical reaction.

One known cartridge dispenses a reagent contained in a reagent reservoir. The cartridge comprises a reservoir which defines an enclosed gas space above the reagent. The cartridge further includes a gas vent that admits, in use, gas to the gas space.

One known microfluidic device for fluid manipulates and analyzes fluid samples. A bellows pump is fluidly connected to a microfluidic channel with a liquid barrier interposed between the bellows pump and an end of the microfluidic channel wherein the liquid barrier is gas permeable and liquid impermeable.

There is a need for to new and improved cartridges for dispensing microfluidic portions of fluids for the purpose of performing an analysis of a biological sample.

SUMMARY

According to the present disclosure, a cartridge for dispensing a fluid, an automatic analyzer and a method of analyzing a biological sample are disclosed. The cartridge can comprise a reservoir chamber operable for receiving the fluid. The reservoir chamber can have a fluid outlet. The cartridge also can comprise a controllable dispenser component for dispensing a dispensing volume of the fluid from the reservoir chamber. The dispenser component can be connected to the fluid outlet of the reservoir. The cartridge can further comprise a compressible fluid pump with an elastic pumping element and a conduit extending from the fluid pump towards the fluid outlet. The fluid pump can discharge a mixing volume of the fluid from the conduit into the reservoir chamber upon compression of the elastic pumping element. The mixing volume can depend on the degree of compression of the elastic pumping element. The fluid pump can suck in the mixing volume from the reservoir into the conduit upon decompression of the elastic pumping element.

Accordingly, it is a feature of the embodiments of the present disclosure to provide new and improved cartridges for dispensing microfluidic portions of fluids for the purpose of performing an analysis of a biological sample. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
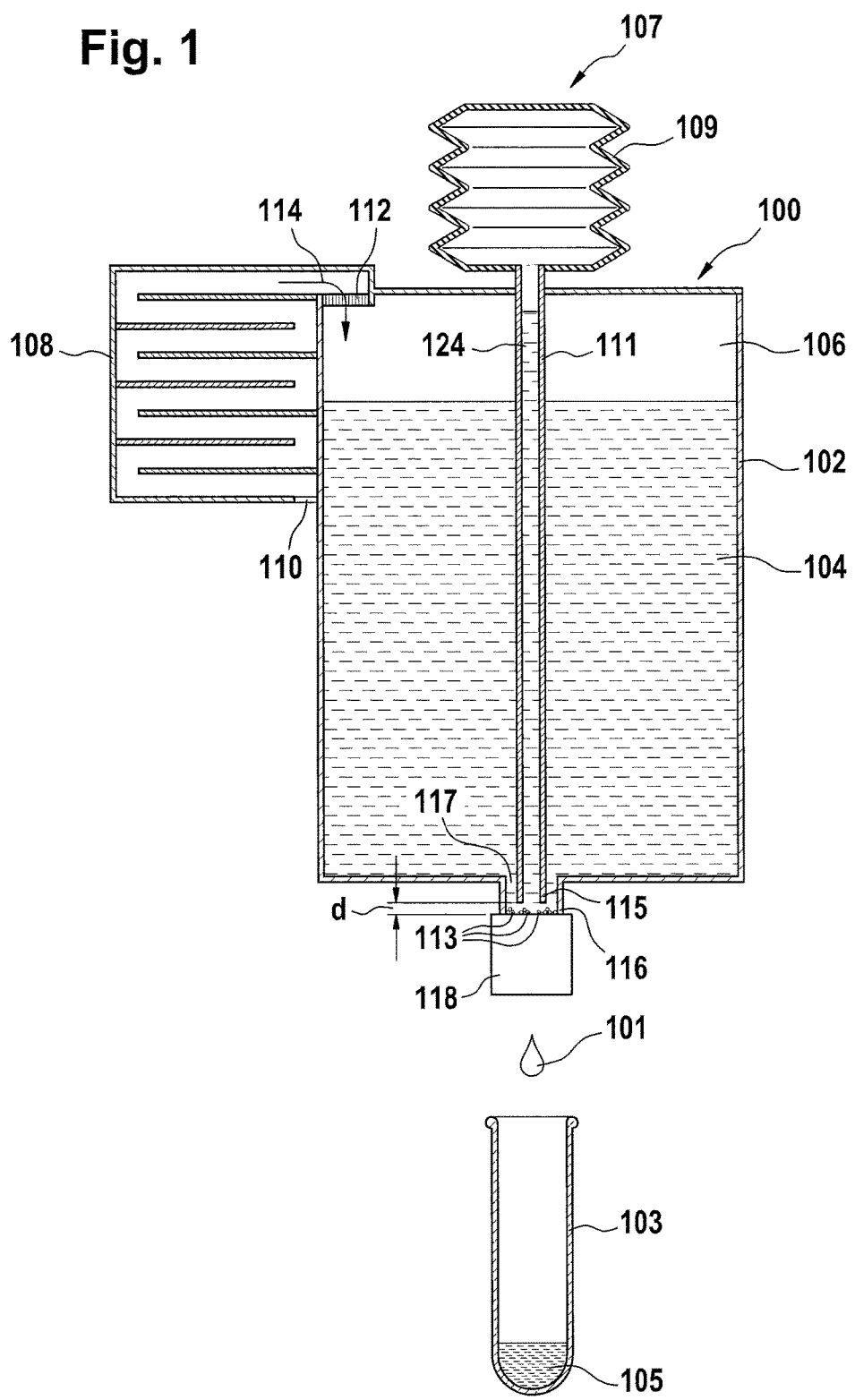
FIG. 1 illustrates a cross-sectional view of an embodiment of the cartridge according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

Embodiments can be particularly advantageous for storing and dispensing a fluid in a suspension containing particles that sediment on a bottom portion of the cartridge. Prior to dispensing a portion of the fluid for the purpose of performing an analysis, the sedimented particles, or at least a portion of the sedimented particles, can be suspended by a fluid flow that can be directed towards the sedimented particles and can mix the particles with the fluid so that the particles can be put back into suspended state. In other words, the sedimented particles can be re-suspended by the fluid caused by discharging a mixing volume from the end of the conduit when the compressible fluid pump is compressed. This can have the advantage that the concentration and distribution of the particles in the fluid fraction of the suspension can reach a predefined level before the dispensing volume is dispensed from the cartridge for the purpose of performing an analysis. This can ensure that the analysis can be performed with a reproducible degree of precision.

Embodiments can be particularly advantageous as no rotating parts may be required for mixing the sedimented particles with the fluid for re-suspending the sedimented particles within the fluid. This can be accomplished by providing a single compressible fluid pump with a single elastic pumping element and an attached conduit extending from the fluid pump towards the fluid outlet which can be particularly beneficial for microfluidic applications. Upon applying pressure onto the elastic pumping element, the elastic pumping element can be compressed, thereby compressing a pumping volume within the pumping element. The pressure on the pumping volume can cause the pumping volume to move towards the conduit which can ultimately lead to a flow of fluid from the conduit.

In this case "elastic" can mean that application of force or pressure onto the pumping element can cause the pumping element to change its shape. However, once the force or pressure vanishes, the pumping element can return to its original shape by itself. Thus, there may be no need for additional steps for preparing the pumping element for a subsequent pumping step. Note that the pumping element may not necessarily have to be made of elastic (that is reversibly deformable) material to be "elastic" as a whole. The pumping element may also be elastic because of its shape, for example, if it is formed by bellows. An example of a pumping element being elastic because of its material can be an elastic membrane.

In accordance with some embodiments, the reservoir chamber of the cartridge can have a bottom portion forming a sink. The sink can comprise the fluid outlet of the reservoir chamber and the conduit extending into the sink for a predetermined distance from the fluid outlet. This can have the advantage of causing a fluid flow locally in this sink area by discharging the mixing volume from the conduit that can be in proximity to the fluid outlet such that the local concentration and distribution of the particles in the suspension can reach its predefined level. During a dispensing step, this portion of the fluid that is in proximity to the fluid outlet can be dispensed such that the dispensing volume can comprise the fluid with the re-suspended particles in a defined concentration range. Another advantage can be that the dead volume can be limited so that the cartridge can remain fully operational even when almost empty due to the fact that any remaining portion of the fluid can be collected in the sink and can thus be mixed by the fluid flow caused by the pumping motion applied to the compressible fluid pump.

In accordance with some embodiments, the cartridge can have a baffle forming a ventilation channel. In accordance with some embodiments, the ventilation channel can have a ventilation volume equal to or larger than the mixing volume that can be dispensed by the fluid pump when the fluid pump is maximally compressed and, therefore, a maximum pumping volume can be displaced by this compression. This can have the advantage of minimizing the influx of ambient gases like oxygen or carbon dioxide from the surrounding atmosphere into the cartridge in order to limit degradation (e.g. by oxygenation) of the fluid contained in the reservoir chamber.

A "cartridge" as understood herein can comprise a receptacle for storing and dispensing a fluid. The cartridge can have a mechanical interface that can match the mechanical interface of a holder of an automatic analyzer. The mechanical interfaces of the cartridge and the automatic analyzer can enable mounting and release of the cartridge to and from the holder such that the cartridge can be conveniently replaced by a new cartridge when the cartridge is empty.

In accordance with some embodiments, the cartridge can comprise a reservoir chamber for receiving and holding the fluid and the reservoir chamber can also be operable for receiving a ventilation gas. The reservoir chamber can comprise an inlet for receiving the ventilation gas. At least a portion of the reservoir chamber can be operable for being filled with the ventilation gas when the cartridge is placed in an operating position. The inlet can be located in the portion operable for being filled with the ventilation gas. The fluid can comprise a reagent. The cartridge can further comprise a baffle for restricting gas diffusion through the inlet. The reservoir chamber can receive the ventilation gas via the baffle. Since the ventilation gas can be provided directly to the gas within the reservoir, there may be no formation of bubbles within the fluid fraction comprised within the reservoir chamber which otherwise can cause variations of the pressure within the reservoir chamber. In accordance with some embodiments, the baffle can provide the ventilation gas directly to the portion of the reservoir chamber operable for being filled with the ventilation gas. Embodiments may therefore have the advantage that there can always be equilibrium in pressure between outside of the cartridge and in the gas within the reservoir chamber. Embodiments may also have the advantage that the baffle can reduce the diffusion of gases into the reservoir chamber which may damage or degrade the fluid (e.g., if the reservoir chamber contains oxygen-sensitive reagents which may degrade by contact with the ambient air). The baffle may also reduce evaporation of the fluid within the reservoir chamber because the diffusion of gas or vapor out of the reservoir chamber can also be reduced.

A "controller" as used herein can encompass a device, machine, or apparatus for controlling the operation and/or function of one or more other devices. Examples of a controller may include, but are not limited to: a computer, a processor, an imbedded system or controller, a programmable logic controller, and a microcontroller. A 'computing device' or 'computer' as used herein can encompass any device comprising a processor. A 'processor' as used herein can encompass an electronic component which may be able to execute a program or machine executable instruction.

A 'hardware interface' as used herein can encompass an interface which can enable a processor or other controller to interact with and/or control an external computing device and/or apparatus. A hardware interface may allow a processor to send control signals or instructions to an external computing device and/or apparatus.

In one embodiment, a cartridge for dispensing a fluid can be provided. The cartridge can comprise a reservoir chamber operable for receiving a fluid and for receiving a ventilation gas. A ventilation gas as used herein can encompass a gas which can be used to equalize the pressure outside of the reservoir chamber and inside the reservoir chamber when fluid is removed from the reservoir chamber. The reservoir chamber can comprise an inlet for receiving the ventilation gas and an outlet for dispensing the fluid. At least a portion of the reservoir chamber can be operable for being filled with the ventilation gas when in an operating position. The inlet can be located in the portion operable for being filled with the ventilation gas. In other words, when the cartridge is in an operating position, ventilation gas can be added to the reservoir chamber at a location where there is already ventilation gas or which can be immediately filled with the ventilation gas. The fluid can comprise a reagent. A reagent as used herein can be a substance or compound that can be added to a (bio-) chemical system in order to initiate or facilitate a chemical or biochemical reaction or to identify or monitor if such a reaction occurs.

In accordance with some embodiments, the cartridge can further comprise a baffle for restricting gas diffusion through the inlet. The reservoir chamber can be operable for receiving the ventilation gas via the baffle. A baffle as used herein can encompass a structure which can cause gas to follow a particular path in order to reach the inlet. The baffle can provide a restriction of the diffusion of gas in and/or out of the inlet. As such the gas diffusion as used herein may refer to the diffusion of ventilation gas into the cartridge and/or gas already present in the reservoir chamber from diffusing out. This embodiment may be advantageous because it may preserve the lifetime of the reagent within the cartridge. For instance, depending upon the reagent constituents, the ventilation gas may cause the reagent to lose effectiveness or to lose its chemical reactivity; also gas inside the reservoir chamber may contain vapors from the fluid. The baffle can restrict the diffusion of the fluid vapor out of the inlet also. This may help to prevent the concentration of a particular reagent from changing.

In another embodiment, the cartridge can comprise a closing element like a cap. The closing element may be operable for being moved into an open position for opening the inlet and/or for enabling access to the pump. In some embodiments, the closing element may seal the inlet directly, that is the sealing effect of the closing element is at the inlet. In other embodiments, the closing element can seal the baffle or a portion of the baffle. This can indirectly seal the inlet.

A closing element as used herein may in some embodiments be a mechanical part operable to open or close the inlet. Examples of closing elements may include, a removable piece of plastic, a piece of tape, and a mechanical part which can be operable to interlock with the cartridge such as a screw cap. Also clamping elements which can close flexible parts of the baffle can be used as closing elements.

In another embodiment, the inlet can be operable for maintaining a constant pressure within the portion of the reservoir chamber that can be operable for being filled with the ventilation gas. This embodiment may be beneficial, because maintaining the pressure at a constant value can enable more accurate dispensing of the fluid. In some embodiments, the inlet can be operable for maintaining a constant pressure within the portion of the reservoir chamber that can be operable for being filled with the ventilation gas when dispensing fluid. For example, an inlet can be submerged within the fluid. Gas can enter into the cartridge reservoir by bubbling at the inlet.

In some embodiments, the ventilation gas may be normal atmospheric air. In some embodiments, the baffle can be open to the atmosphere.

In another embodiment, the closing element can be operable for being moved to an open position to open the inlet. The closing element may be removable or may be movable but fixed to the cartridge.

In another embodiment, the cartridge can further comprise the fluid. i.e., is in a filled state.

In another embodiment, the fluid can comprise a dispersion or suspension. A dispersion or suspension as used herein can encompass particles or particulates suspended within the fluid.

In another embodiment, the fluid may comprise latex particles.

In another embodiment, the fluid may comprise nanoparticles.

In another embodiment, the fluid may comprise magnetic particles.

In another embodiment, the cartridge can further comprise a dispenser for dispensing the fluid. The dispenser can be operable for receiving the fluid from the outlet of the reservoir chamber. In some embodiments, the dispenser may be a microfluidic dispenser for dispensing a microfluidic portion of the fluid. In other embodiments, the dispenser may comprise a nozzle. For instance, the dispenser may comprise a straight tube or may comprise a nozzle with one or more valves contained within it.

In another embodiment, the dispenser can be operable to dispense fluid at a rate independent of the baffle. In other words, the dispensing of the fluid may not be regulated or controlled by the baffle.

For example, an apparatus can controllably release a substance. A regulator element can restrict the flow of gas into the apparatus and can effectively control the release rate of a fluid. In contrast to this, in some embodiments, fluid can be dispensed at a rate that can be effectively independent of the baffle. The baffle, according to some embodiments, may have such a small effect on the rate of dispensing that the effect is much smaller than the actual volume dispensed. This may enable more accurate dispensing of the fluid.

In another embodiment, the dispenser can be a microfluidic dispensing assembly.

In another embodiment, the dispenser can be operable for dispensing any one of the following: volumes less than 10 μL, less than 500 nL, less than 200 nL, less than 100 nL, and less than 20 nL.

An automatic analyzer for holding or receiving a cartridge according to an embodiment is also presented. The automatic analyzer can comprise an actuator assembly operable for actuating the dispenser. The automatic analyzer can also comprise an actuator assembly operable for actuating the fluid pump. The automatic analyzer can further comprise a controller for controlling the operation of the actuator assembly and the fluid pump.

The dispenser and the fluid pump may be mechanically, pneumatically, magnetically, and/or electrically actuated. This can be dependent upon the implementation and how the dispenser can be constructed. In one embodiment, the cartridge can be in an operating position when installed into the automatic analyzer.

Referring initially to FIG. 1, FIG. 1 illustrates a cartridge 100 according to an embodiment. The cartridge 100 can comprise a reservoir chamber 102 for holding a fluid 104. The reservoir chamber 102 can only be partially filled with the fluid 104. There can be a region filled with gas 106, such as air, at the top of the reservoir chamber 102.

Adjacent to the reservoir chamber 102 can be a baffle 108. The baffle 108 in this example can have a vent-to-atmosphere 110. Traveling through the baffle there can be an optional gas filter 112 which can cover an inlet 114 to the reservoir chamber 102. The inlet 114 can provide ventilation gas to the gas filled portion 106 of the reservoir chamber 102. The inlet 114 can be attached to the baffle 108.

The fluid 104 can exit the reservoir chamber 102 via an outlet 116. In this example, there can be a dispenser 118. The dispenser 118 may comprise a nozzle or tube for dispensing the fluid when it can be actuated by an external device, such as by an actuator assembly of an analyzer (see, for example, FIG. 5).

The dispenser 118 can serve for dispensing a dispensing volume 101 into a receptacle 103. For example, the dispensing volume 101 of a reagent fluid contained within the reservoir chamber can be mixed with a biological sample 105 contained in the receptacle 103 for performing an analysis for detecting an analyte.

The dispenser 118 can be connected to the fluid outlet 116 of the reservoir chamber 102.

The cartridge 100 can have a fluid pump 107 that can comprise bellows 109 forming an elastic pumping element outside the housing of the cartridge 100. The bellows 109 can be connected to a conduit 111 that can extend from the bellows towards the fluid outlet 116.

In one embodiment, the fluid 104 can be a suspension containing particles. A portion of the particles, i.e. particles 113, can form sediment on a bottom portion of the reservoir chamber 102. In order to re-suspend the sedimented particles 113, the bellows 109 can be compressed such as by an actuator of an analyzer that holds the cartridge 100 (see, for example, FIG. 5) (or in an alternative element also manually), such that a mixing volume 124 of fluid can be discharged from the end portion 115 of the conduit 111 that can cause a fluid flow mixing the sedimented particles 113 with the fluid 104, thus re-suspending the particles 113.

When the bellows 109 are released, they can decompress and suck in the previously discharged mixing volume 124 from the fluid 104 contained in the reservoir chamber 102 to prepare for the next mixing cycle.

In accordance with one embodiment, the conduit 111 can be tube- or pipette-shaped as shown in FIG. 1. Alternatively, the conduit 111 may have a curved form. For example, the bellows 109 may be arranged on a side of the housing of the cartridge 100 rather than on the top. In this instance, the geometry of the cartridge 100 may require the conduit 111 to have a curved form.

In one embodiment, the reservoir chamber 102 can have a bottom portion that can form the sink 117 which can comprise the fluid outlet 116. The conduit 111 can extend into the sink 117 to a predetermined distance d from the fluid outlet 116. For example, the distance d may be in the range of about 1 mm to about 10 mm. In one embodiment, the distance d can be about 3 mm. This can have the advantage that the fluid flow that can be caused by discharging the mixing volume from the end portion 115 of the conduit 111 can be concentrated within the sink 117 for re-suspending the sedimented particles 113 that have sedimented on the bottom of the sink 117. This can cause an intense mixing and re-suspending of the particles in this portion of the reservoir chamber. In a next step after finalization of the mixing process, a portion of the fluid 104 that is in the sink 117 can be dispensed as dispensing volume 101 by the dispenser 118.

In accordance with some embodiments, the reservoir chamber 102 and the pump that can be constituted by the bellows 109 and the conduit 111 can be a single form piece, such as an injection molded piece, that can be produced such as by two component injection molding. For example, the reservoir chamber 102 may comprise polypropylene and the pump, i.e. the bellows and the conduit 111, may comprise polyethylene. In still another embodiment, the bellows may be a single form piece with the cover of the cartridge.

The particles 113 contained in the fluid 104 may comprise magnetic beads such as streptavidine-coated magnetic beads that may be required for performing an electrochemiluminescence analysis. In alternative embodiments (e.g. for clinical chemistry tests), also coated latex particles can be used as particles 113. The fluid 104 may be any particle enhanced immunoassay reagent comprising suspended particles that may sediment after some storage time.

In accordance with one embodiment, the volume of air contained in the baffle 108 can be equal or larger than the maximum mixing volume 124 that can be discharged when the bellows 109 are maximally compressed. This can be to avoid or reduce the influx of air from the surrounding atmosphere into the reservoir chamber 102 when a pumping cycle is executed.

Figure 6:
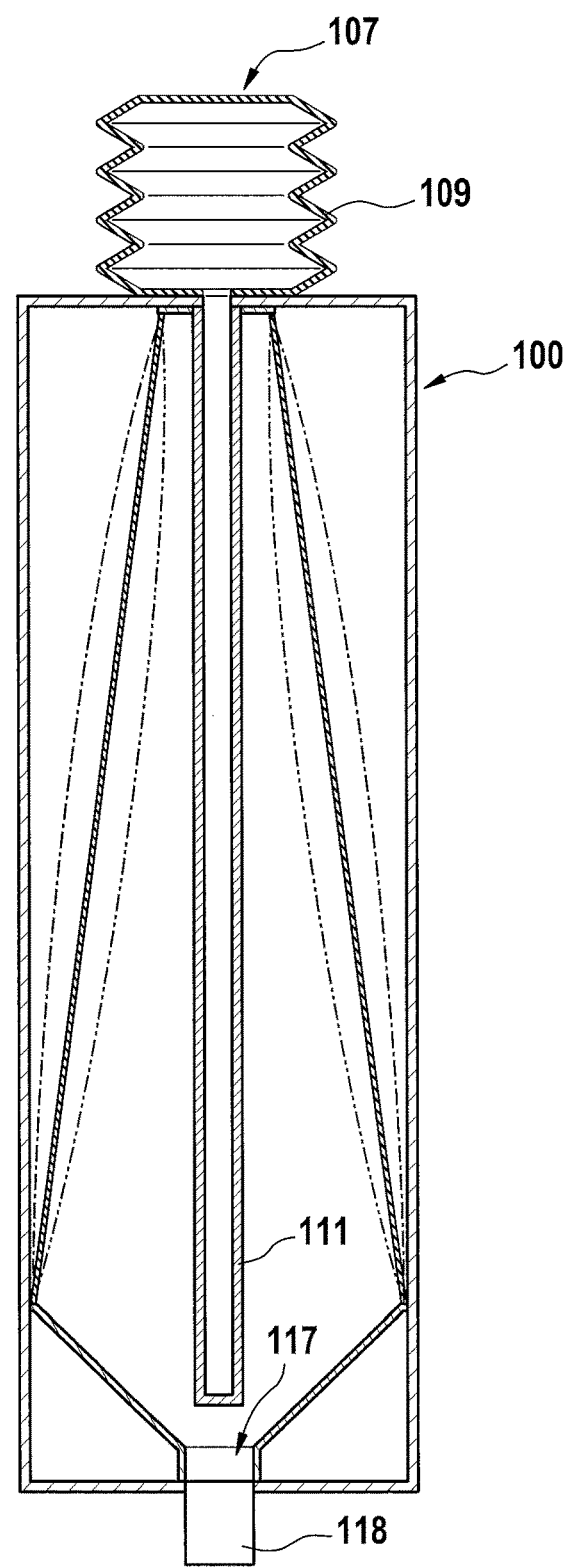
FIG. 6 illustrates the cartridge without a baffle and flexible reservoir chamber walls according to an embodiment of the present disclosure.

In accordance with other embodiments, the walls of the reservoir chamber can be flexible. These walls can expand when the fluid pump is compressed (and the additional mixing volume is pressed into the reservoir chamber) and can shrink when the fluid pump is decompressed and when fluid 104 is dispensed so that no baffle is required. Such an embodiment without a baffle is shown in FIG. 6. The dashed lines show the variation of the volume of the reservoir chamber 102 during a pumping cycle.

Figure 2:
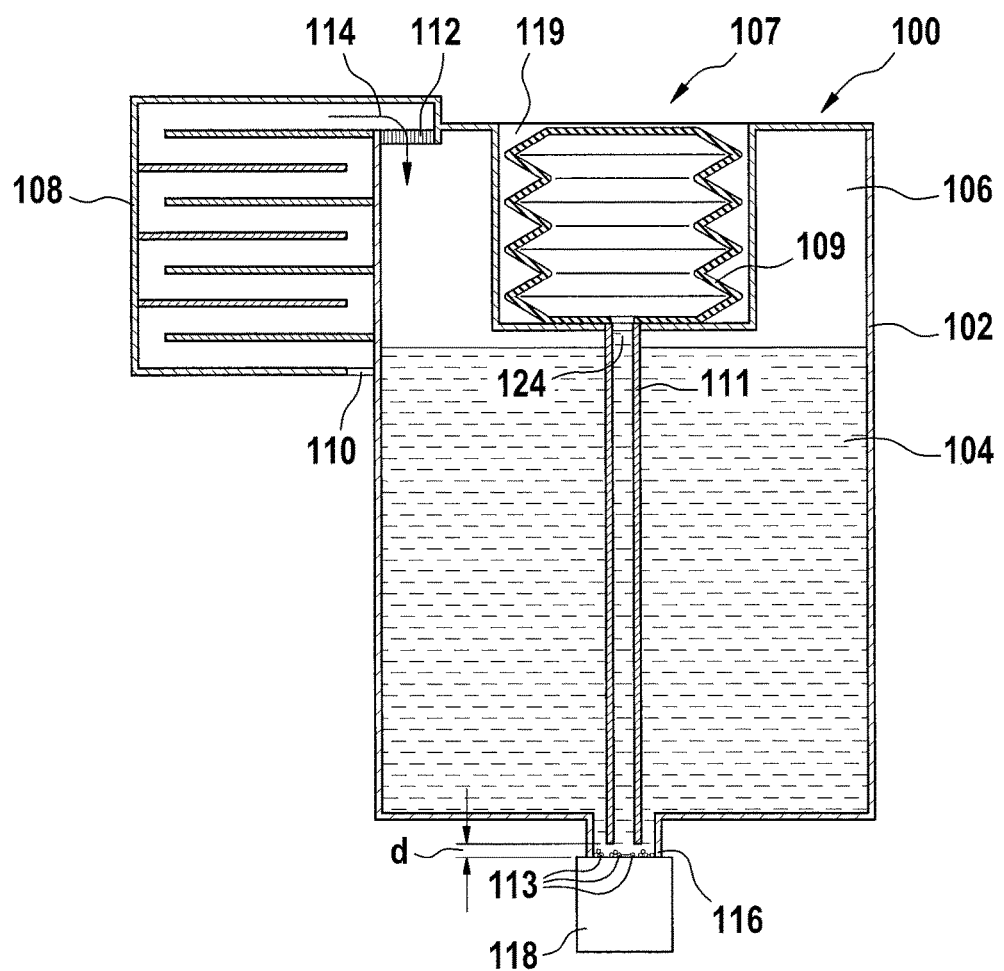
FIG. 2 illustrates the cartridge where the bellows are integrated into the housing of the cartridge according to another embodiment of the present disclosure.

FIG. 2 shows an alternative embodiment where the bellows 109 are integrated within the housing of the cartridge 100. The housing of the cartridge 100 may have a top portion with an opening 119 through which the bellows 109 can be accessible for compression. For example, an actuator of an automatic analyzer can be inserted into the opening 119 for compressing the bellows 109. As a further alternative, a cap as a closing element may be placed into or onto the opening 119 for transportation of the cartridge 100. The cap can be removed from the opening 119 when the cartridge 100 is put into a holder of the automatic analyzer. Removal of the cap may also open the vent to atmosphere 110. The embodiment of FIG. 2 can have the advantage that the pumping element defined by the bellows can be integrated within the housing of the cartridge for easier packaging, transportation, mounting and releasing from the holder of the analyzer.

Figure 3:
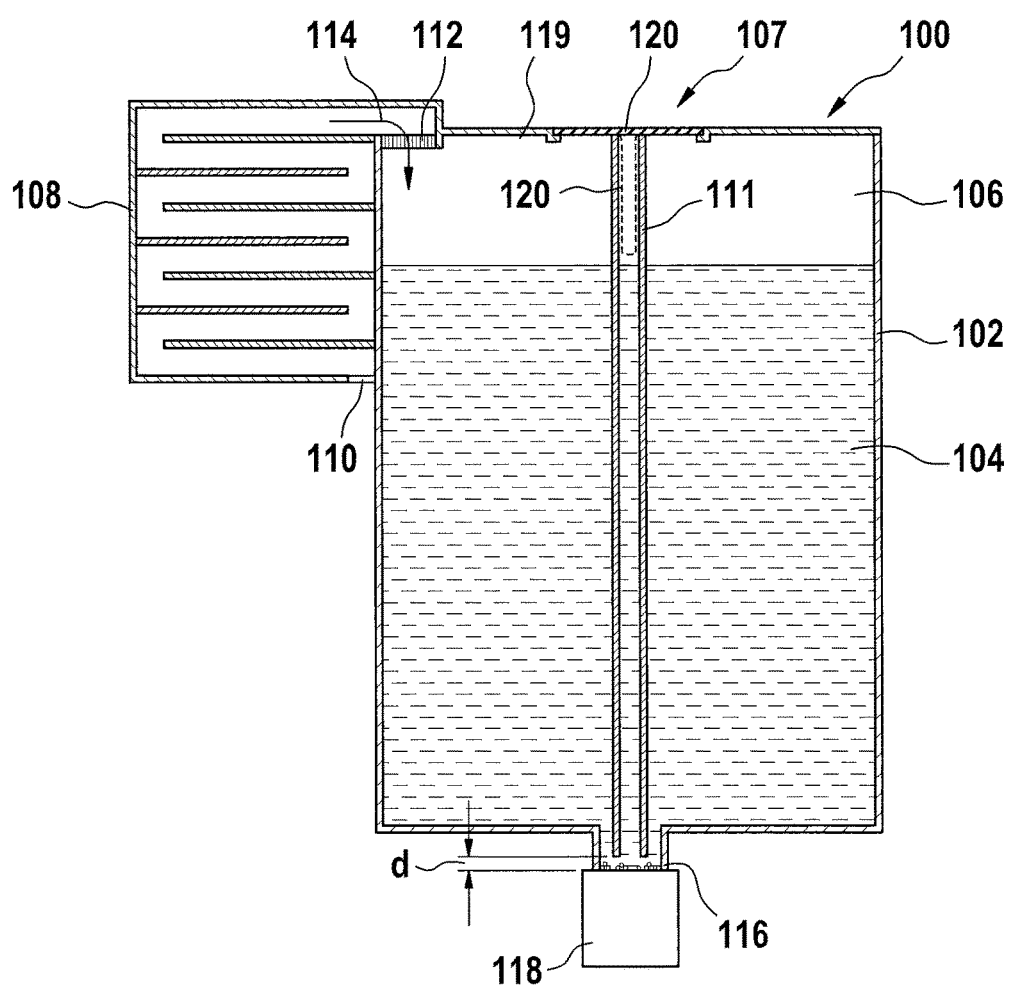
FIG. 3 illustrates the cartridge having a membrane instead of bellows according to another embodiment of the present disclosure.

FIG. 3 shows a further embodiment of the cartridge 100 where the elastic pumping element can be an elastic membrane 120. By an external actuator, the membrane 120 can be deformed to extend into the inside of the conduit 111 for compressing the pumping volume as shown by the dotted lines in FIG. 3.

Figure 4:
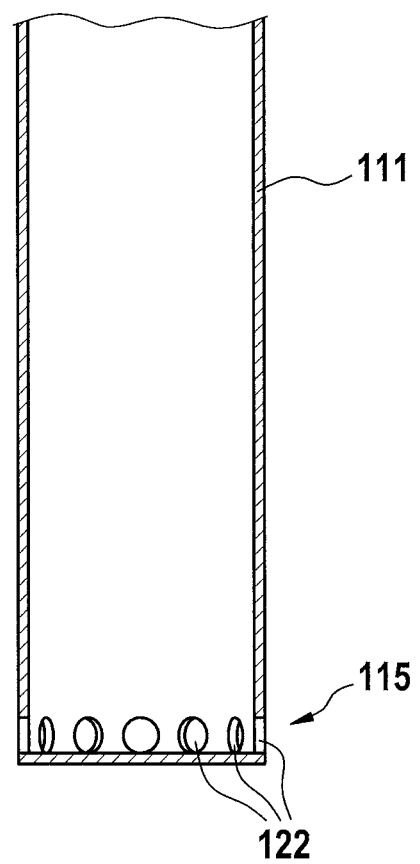
FIG. 4 illustrates schematically an end portion of a conduit according to an embodiment of the present disclosure.

FIG. 4 shows an end portion 115 of the conduit 111. The end portion 115 can have openings 122 that can spread around the perimeter of the end portion 115 of the conduit 111. The end of the conduit 111 that faces the fluid outlet 116 may be closed such that the mixing volume can be discharged through the openings 122 for causing a maximum swirl and mixing effect.

Figure 5:
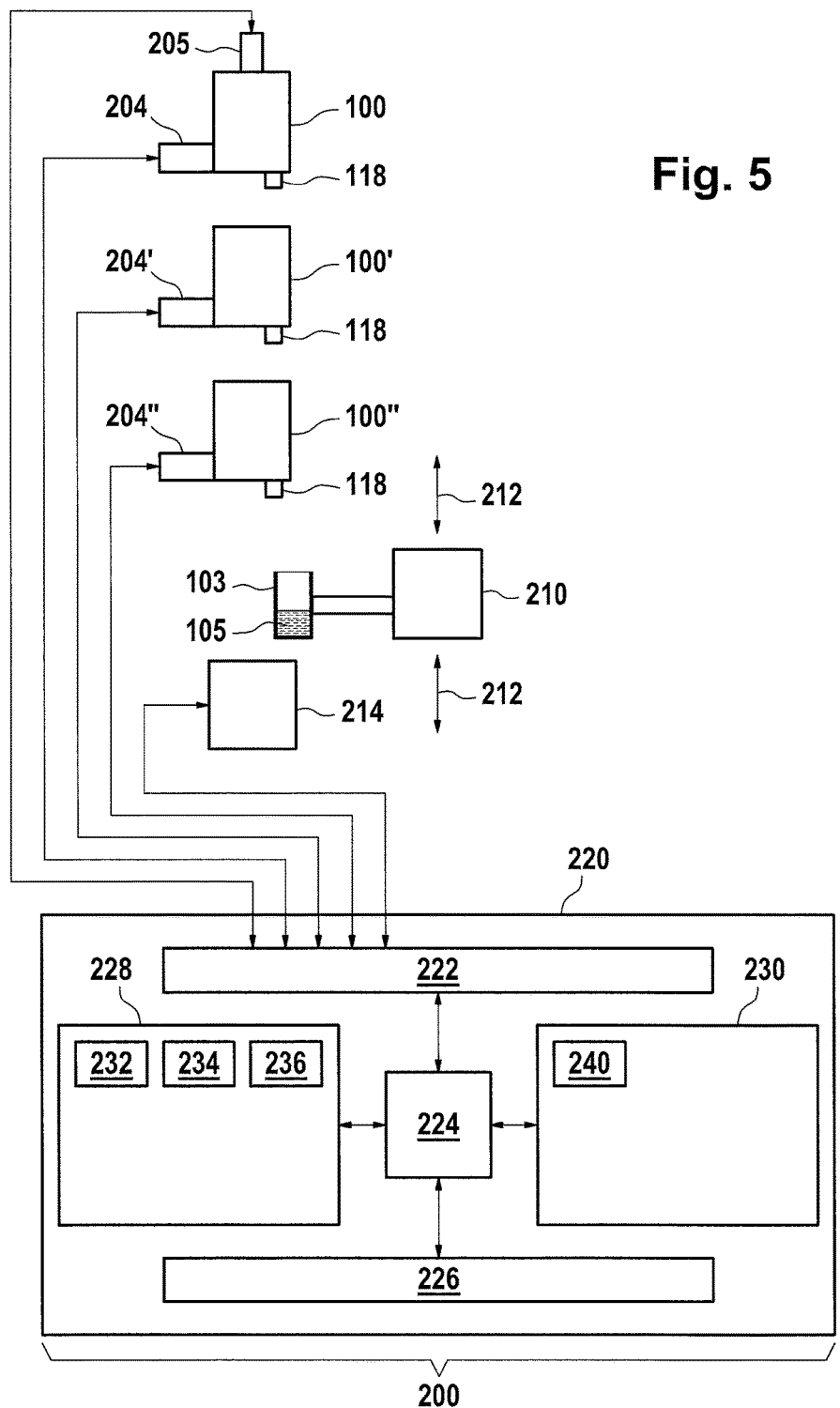
FIG. 5 illustrates a block diagram of an automatic analyzer according to an embodiment of the present disclosure.

FIG. 5 illustrates an automatic analyzer 200 according to one embodiment. This automatic analyzer is shown as having three cartridges 100, 100' and 100". At least one of the cartridges, such as cartridge 100, can contain the fluid 104 with suspended and partly sedimented particles 113 in accordance with the embodiments of the FIGS. 1 to 4. The other cartridges 100' and 100" may be of identical or similar design and may contain fluids without sedimenting particles thus not requiring the compressible fluid pump of the FIGS. 1 to 4 embodiments.

There can be an actuator assembly 204 connected to cartridge 100. There can be an actuator assembly 204' attached to cartridge 100'. There can be an actuator assembly 204" attached to cartridge 100". The actuators 204, 204', 204" can be for actuating the dispenser 118 of the cartridges 100, 100', 100".

The automatic analyzer 200 is shown as having a relative mover 210 which can provide relative movement 212 between a receptacle 103 and the cartridges 100, 100' and 100". The receptacle 103 is shown as containing a biological sample 105. The cartridges 100, 100', 100" may be used to add one or more fluids to the biological sample 105. The automatic analyzer 200 may optionally comprise a measurement system 214. The measurement system may comprise one or more sensors for measuring a physical quantity or physical property of the biological sample 105. For example, the measurement system 214 may comprise an NMR system, an optical transmission or reflectance measurement system, an electrochemical or optical sensor, a pH meter, a camera system or a chromatography system. The relative mover 210 can also be operable for moving the receptacle 103 to the measurement system 214.

The arrangement of the cartridges 100, 100', 100" and the measurement system 214 is representative. The measurement system 214 may be alternatively also a part of the receptacle 103. In some embodiments, the receptacle 103 may remain in a fixed position and the cartridges 100, 100', 100" may move. The actuation systems 204, 204', 204" and the measurement system 214 are shown as being connected to a hardware interface 222 of a computer system 220. The computer system 220 can function as a controller for the automatic analyzer 200.

The computer 220 is further shown as containing a processor 224 which can be able to control the operation and function of the automatic analyzer 200 using the hardware interface 222. The processor 224 is shown as being connected to a user interface 226, computer storage 228 and computer memory 230. The computer storage 228 is shown as containing an analysis request 232. The analysis request 232 can contain a request to analyze the biological sample 105.

The computer storage 228 is shown as containing sensor data 234 received from the measurement system 214. The computer storage 228 is shown as containing an analysis result 236 which may be determined using the sensor data 234. The computer memory 230 can contain a control module 240. The control module 240 can contain computer executable code which can enable the processor 224 to control the operation and function of the automatic analyzer 200. For instance, the control module 240 may use the analysis request 232 to generate commands to generate and send to the actuation systems 204, 204', 204", the measurement system 214 and the relative movement system 210. The control module 240 may also generate the analysis result 236 using the sensor data 234.

The automatic analyzer 200 can have an additional actuator assembly 205 that can be coupled to the cartridge 100. The actuator assembly 205 can act upon the compressible fluid pump of the cartridge 100, e.g. on the bellows 109 (see FIG. 1 and FIG. 2) or on the elastic membrane 120 (see FIG. 3) if it receives a respective control signal from the control module 240.

It can be important to note that the cartridges 100, 100' and 100" can be releasably held by the automatic analyzer 200 for convenient replacement if they are empty and for directly dispensing from the cartridges without pipetting.

In operation, the automatic analyzer that holds the cartridges 100, 100' and 100" can perform the following steps for analyzing the biological sample 105:

a) The computer system 220 can control the relative mover 210 to place the receptacle 103 underneath the dispenser 118 of the cartridge 100.

b) The computer system 220 can control the actuator assembly 205 that can be coupled to the cartridge 100 to compress the elastic pumping element of the fluid pump of the cartridge 100 such that any particles 113 of the fluid 104 that may have sedimented can be re-suspended due to the mixing that can be caused by discharging the mixing volume 124 (see FIGS. 1 to 3) from the conduit 111. Such a compression/depression cycle of the elastic pumping element can be repeated multiple times to ensure a defined and reproducible mixing of the particles within the fluid.

c) The actuator assembly 204 can be controlled by the computer system 220 to act upon the dispenser 118 to dispense a required amount of the fluid 104 into the receptacle 103 for mixing with the biological sample 105.

In the following, the computer system 220 may control the relative mover 210 to place the receptacle 103 under the dispensers 118 of the cartridges 100' and 100" for dispensing respective amounts of fluids from the cartridge 100' and 100" into the receptacle 103. Depending on the kind of analysis that is performed, such as an electrochemiluminescence analysis, incubation can be performed before a measurement step that can be executed by the measurement system 214 for determination of the presence of an analyte within the biological sample 105.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A cartridge for dispensing a fluid, the cartridge comprises:
    a reservoir chamber for receiving the fluid, the reservoir chamber having a fluid outlet;
    a controllable dispenser component for dispensing a dispensing volume of the fluid from the reservoir chamber, the dispenser component being connected to the fluid outlet of the reservoir;
    a single compressible fluid pump with a single elastic pumping element; and
    a conduit extending from the fluid pump towards the fluid outlet,
    wherein the fluid pump being operable to discharge a mixing volume of the fluid from the conduit into the reservoir chamber upon compression of the elastic pumping element, the mixing volume depending on the degree of compression of the elastic pumping element, and the fluid pump being operable to suck in the mixing volume from the reservoir into the conduit upon decompression of the elastic pumping element.

2. The cartridge according to claim 1, wherein the elastic pumping element is formed by bellows.

3. The cartridge according to claim 1, wherein the elastic pumping element is an elastic membrane.

4. The cartridge according to claim 1, wherein the conduit is tube or pipette-shaped.

5. The cartridge according to claim 1, wherein the reservoir chamber has a bottom portion forming a sink.

6. The cartridge according to claim 5, wherein the sink comprises the fluid outlet of the reservoir chamber and wherein the conduit extends into the sink to a predetermined distance (d) from the fluid outlet.

7. The cartridge according to claim 6, wherein the distance d is in the range of 1 mm to 10 mm.

8. The cartridge according to claim 6, wherein the conduit has an end portion facing the outlet, the end portion having multiple openings spread around a perimeter of the end portion for discharging the mixing volume.

9. The cartridge according to claim 1, wherein the reservoir chamber further comprises an inlet for receiving a ventilation gas and a baffle for restricting gas diffusion through the inlet.

10. The cartridge according to claim 9, wherein the baffle forms a ventilation channel, the ventilation channel having a ventilation volume equal to or greater than the mixing volume that results from a maximum compression of the elastic pumping element.

11. The cartridge according to claim 1, wherein the reservoir chamber has walls that are flexible.

12. The cartridge according to claim 11, wherein the reservoir chamber is designed to expand upon compression of the elastic pumping element and to shrink upon decompression of the elastic pumping element.

13. The cartridge according to claim 1, wherein the reservoir chamber is at least partly filled with the fluid, the fluid being a dispersion or a suspension containing particles that sediment on a bottom portion of the reservoir.

14. The cartridge according to claim 13, wherein the particles are magnetic beads and/or latex-beads.

15. The cartridge according to claim 14, wherein the magnetic beads are magnetized polystyrene beads having a diameter between 1 µm and 4 µm and the latex-beads have a diameter between 0.05 µm and 0.4 µm.

16. The cartridge according to claim 14, wherein the beads are streptavidin-coated for binding a biotinylated antibody.

17. An automatic analyzer for analyzing a biological sample, the automatic analyzer comprising:
- a holder for holding the cartridge in accordance with claim 1 in an operating position;
- a first actuator assembly for actuating the dispenser component of the cartridge for controlling the dispenser component to dispense the dispensing volume; one or more sensors for measuring a physical quantity or physical property of the biological sample;
- a second actuator assembly for compressing the elastic pumping element of the cartridge; and
- a controller for controlling the second actuator assembly for compressing the elastic pumping element prior to controlling the first actuator assembly for dispensing the dispensing volume.

* * * * *